United States Patent [19]

Meyers et al.

[11] 4,135,497

[45] Jan. 23, 1979

[54] APPARATUS FOR DETECTING TEMPERATURE VARIATIONS OVER SELECTED REGIONS OF LIVING TISSUE, AND METHOD THEREOF

[75] Inventors: Phillip H. Meyers, New Orleans, La.; Franklin R. Greene, Flushing, N.Y.

[73] Assignee: E-Z-EM Company, Inc., Westbury, N.Y.

[21] Appl. No.: 779,264

[22] Filed: Mar. 18, 1977

[51] Int. Cl.² ............................................. A61B 10/00
[52] U.S. Cl. ...................................... 128/2 H; 73/356
[58] Field of Search ....................... 128/2 H, 280–282, 128/379, 399–401, 88, 89; 73/356

[56] References Cited

U.S. PATENT DOCUMENTS

| | | | |
|---|---|---|---|
| 3,533,399 | 10/1970 | Goldberg et al. | 73/356 |
| 3,674,031 | 7/1972 | Weiche | 128/303.1 |
| 3,847,139 | 11/1974 | Flam | 128/2 H |
| 3,859,982 | 1/1975 | Dove | 128/2 R |
| 3,951,133 | 4/1976 | Reese | 128/2 H |
| 3,993,809 | 11/1976 | Schranz et al. | 128/2 H |
| 3,995,621 | 12/1976 | Fletcher et al. | 128/2 H |
| 3,998,210 | 12/1976 | Nosari | 128/2 H |
| 4,015,591 | 4/1977 | Suzuki et al. | 128/2 H |
| 4,024,856 | 5/1977 | Kirianoff | 128/2 S |
| 4,043,324 | 8/1977 | Shaw | 128/68 X |

FOREIGN PATENT DOCUMENTS 1,354,874  5/1974  United Kingdom .................... 128/2 H

OTHER PUBLICATIONS

"The Chameleon Chemical," Life Magazine.

Primary Examiner—Robert W. Michell
Assistant Examiner—Francis J. Jaworski
Attorney, Agent, or Firm—McAulay, Fields, Fisher & Goldstein

[57] ABSTRACT

An apparatus for detecting temperature variations over selected regions of living tissue. The invention relates to the apparatus and to the method of detecting said temperature variations for aid in the early detection of malignant tissue in the breasts. The invention provides for the use of liquid crystals encapsulated between elastic flexible sheets which represent a composite film. The crystals are responsive to changes in temperature of said tissue to display a color pattern on said film representative of said temperature variations. The film conforms to the contour of the tissue to which it is applied, without materially deforming said tissue, by evacuating air from between said film and said tissue. The color pattern produced on said film is observed and is recorded photographically to obtain a thermogram of said temperature variations. The contoured film and the tissue are fan cooled for a relatively short period of time to produce a more sensitive color pattern on said film representative of said temperature variations.

16 Claims, 4 Drawing Figures

APPARATUS FOR DETECTING TEMPERATURE VARIATIONS OVER SELECTED REGIONS OF LIVING TISSUE, AND METHOD THEREOF

BACKGROUND OF THE INVENTION

1. Field of the Invention

This invention relates generally to an apparatus for detecting temperature variations over selected regions of a living tissue, and to a method of detecting said temperature variations. The technique utilizes an encapsulated liquid crystal film that conforms to the contour of the tissue by evacuating air from between said film and said tissue. The crystals are responsive to changes in temperature of said tissue to display a color pattern on said film representative of said temperature variations.

2. Description of the Prior Art

Thermography, in its broadest sense, is a technique for detecting and measuring variations in the heat emitted by various regions of the body and transforming them into visible signals that can be recorded photographically. The technique is lately experiencing increased interest as a potentially significant aid in diagnosing abnormal or diseased underlying conditions, particularly those involving cancer of the breast.

At present, progress in the treatment of cancer of the female breast lies mainly in the area of early detection, with the diagnosis made and treatment instituted at an early stage of the disease. Although frequent physical examinations are recommended by the medical community, it is recognized that malignant tumors detected by this technique are often of such size as to indicate that the malignancy has already spread to other areas of the body. In order to provide earlier detection of the disease, much emphasis has also been placed on radiographic mammography. However, since this technique involves X-ray examinations, there is the danger of exposing the patient to excessive radiation. Mammography further requires the use of sophisticated equipment that is extremely costly, and the assistance of technically skilled personnel.

In recent years, significant scientific progress has been made in the use of thermography as an added instrument of diagnosis. All methods of thermographic examination are based on the fact that malignant neoplasms are surrounded by an extraordinarily large number of blood vessels. This serves to explain localized rises in temperature, stemming from the increased blood flow and metabolic activity, which are transmitted to the overlying skin surface. All work using thermography has been directed toward diagnosis by means of the differences in temperature of points or areas on the skin. For example, the skin temperature of the breast on the side with a tumor is found to be more than 1° C. higher than that on the healthy side. Advanced carcinomas were warmer still, and it is possible to deduce the severity of the condition from the raised temperature.

Initial work with this technique was in the area of electronic infra-red thermography (EIT). This is a method of remote sensing of the infra-red radiation emitted by the surface of the breast. The scientific community was not entirely satisfied with this technique because of its limited reliability and the difficulty of interpreting the results. In this regard, the early equipment did not provide reliably informative thermograms in recording the small temperature differential between the tumor side and the healthy side of the breast. Furthermore, the slight temperature variations might well be caused by other conditions unrelated to the tumor. For example, the effects of the menstrual cycle, of hormonal contraceptives and of pregnancy have been found to cause minor day-to-day temperature changes which must be taken into consideration when reading the thermogram. Thus, it became accepted practice in the medical community that EIT, on its own, gave too many false-positive diagnoses, and that only a concurrent mammographic examination would allow greater certainty in diagnosing the condition as benign or malignant. The equipment required in practicing EIT was also extremely costly and often required the assistance of skilled personnel.

Continued research brought forth the development of liquid crystal thermography to obtain a multi-colored recording of the body region under examination. The liquid crystalline state is a particular form of matter lying midway between the solid crystal and a normal (iostropic) liquid. The use of liquid crystals in thermography evolved when it was determined that certain cholesterine esters with the properties of liquid crystals had the ability to react to variations in temperature by changing color. It soon became apparent that such cholesteric liquid crystals (CLC) might be used in science and technology as a temperature indicator.

The initial procedures practiced in the use of liquid crystals were extremely complicated and burdensome for the patient. In view of the fact that the temperature indicators had to be on a black background in order to show their color reaction with sufficient clarity, the patient's skin first had to be painted with a black undercoat, onto which the liquid crystals were then applied with a brush. The color reactions that ensued were visible only by daylight and were recorded by a camera on color film. Apart from the impracticality of this procedure for mass screening or routine examinations, it also has the disadvantage that the liquid crystals can be used only once. An additional problem with this technique is that it does not reproduce accurately the local vascular features. Moreover, the brushing technique is time-consuming and uncomfortable for the patient. Furthermore, heat diffusion causes unsharpness of detail in the images obtained thereby preventing a reliable diagnostic interpretation.

The technology further evolved to the point where the liquid crystals are now encapsulated in plates. The encapsulated liquid crystals (ELC), which form the basis of plate thermography, offers the advantage of changing the liquids into pseudo-solids, and improves the handling and processing of the liquid crystals. The plate registers temperature differences by means of the color reactions produced by the encapsulated cholesterine-type fluid crystals. As temperature rises, the reactions run through the color scale from red to green to blue, and the individual shades are able to indicate temperature differences of 1/10th of a degree centigrade. The color reactions take place a few seconds after the plate has been placed against the subject to be examined. The reaction is also reversible with equal rapidity in that the colors disappear quickly when the plate is removed from the subject to be examined.

Although the plate records zones of differing temperature with a relatively sharp outline, the use of plate thermography is still pretty well confined to clinical research facilities and/or use thereof in the doctor's office. The equipment is not suitable for use directly by the patient in her home, and is not sufficiently portable for use outside of the doctor's office.

Furthermore, because the plate is fairly rigid, it is not possible to shape it to the contour of the breast being examined. Thus, in examining the female breast, it is normal to diagrammatically divide the breast into four quadrants and then apply the plate separately to each one of the quadrants. A lateral view can also be obtained by having the patient turn sideways and applying the plate while the arm is raised. Color photographs can be taken of the color pattern produced on the plate. It will be readily appreciated that, due to the curvature of the breast, it is not possible to examine the breast with the use of only one plate. In this regard, it is important not to materially deform the tissue which is in contact with the plate since this would serve to distort the thermogram and thereby prevent a reliable diagnostic interpretation.

It thus became apparent that greater utility in the field of liquid crystal thermography would be possible if the plates were rendered flexible. The technology soon evolved to the use of such flexible plates in the form of thin plastic sheets superimposed on each other to form a composite film having the liquid crystals encapsulated therebetween. The construction may be deemed as representing micro-encapsulated liquid crystals sandwiched between two polyester sheets or substrates. The film is capable of being manufactured so as to be responsive to selective temperatures within a particular range of temperatures. This is a function of the crystals selected for use in the film. In other words, the crystals are selected so that they are operative in a temperature range that encompasses foreseen variations of body temperature in the region of the body under examination. The method of manufacturing such films is readily disclosed in the prior art as evidenced by U.S. Pat. Nos. 3,619,254 and 3,969,264.

Today, thermography using liquid crystals is receiving additional interest in diagnosing changes in venous and arterial blood vessels, bone and thyroid gland diseases, dermatological examinations, and in other clincial and physiological investigations.

In some applications, the initial thermographic test is then followed by another with the skin pre-cooled with cool air from a hand blower. The objective in this technique is to exclude the pronounced degree of heat formation and vascular visualization from physiological causes that is an almost regular feature of the sexually mature woman and of one receiving hormone medication. The thermographic images that result from this could well mask a pathological vascular picture. However, the areas of heat or vascular features stemming from pathological causes will reappear more rapidly than normal vascularization after cooling of the breast, or else will not disappear in the first place.

The use of liquid crystal thermography as an aid in detecting changes in the temperature of the skin, and particularly in detecting breast cancer, is noted in U.S. Pat. Nos. 3,830,224 and 3,847,139. In each of these patents, the liquid crystals are incorporated into the body of a garment, such as a brassiere, which is intended to conform essentially to the contour of the breasts. While the devices respectively disclosed in these patents produce a meaningful thermogram over certain regions of the breast, they have not proven satisfactory as an aid in diagnosing the condition of the entire breast. In this regard, it is important that the crystals be in contact with the entire region to be examined. The disclosed brassieres do not satisfy this requirement. In some instances, depending on the size and shape of the woman's breasts, some of the portions of the brassiere do not come in contact with the breasts at all while other portions contact the breasts to such an extent as to deform the breasts thereby producing a distorted thermogram. Furthermore, the brassieres have the tendency to hide or mark the sides of the breasts to prevent a reliable diagnostic examination. The present invention eliminates the objections and disadvantages present in using the aforesaid brassiere garments by providing an improved apparatus, and method of using the same, which causes the film to effectively conform to the contour of the entire breast without materially deforming said breast.

SUMMARY OF THE INVENTION

The invention provides for use of liquid crystals encapsulated between elastic flexible sheets which represent a composite film. The crystals are responsive to changes in temperature of the tissue against which the film is brought in contact with to display a color pattern on said film representative of said temperature variations. The film conforms to the contour of the tissue to which it is applied, without materially deforming said tissue, by evacuating air from between said film and said tissue. The color pattern produced on said film is observed and is recorded photographically to obtain a thermogram of said temperature variations. The contoured film and the tissue may also be fan cooled for a relatively short period of time to produce a more sensitive color pattern on said film representative of said temperature variations.

Accordingly, an object of the present invention is to provide an apparatus for detecting temperature variations over selected regions of living tissue within a predetermined range of temperatures.

Another object of the present invention is to provide an apparatus for aid in the early detection of malignant tissue in the breasts of a woman.

A further object of the present invention is to provide a method of detecting temperature variations over selected regions of a woman's breast, within a predetermined range of temperatures, by causing encapsulated liquid crystal film to conform to the contour of the breast without materially deforming said breasts to produce a color pattern on said film representative of said temperature variations.

Another object and feature of the present invention is to provide an apparatus for detecting temperature variations over selected regions of living tissue, which apparatus is relatively inexpensive and which may be used without the need of highly trained personnel.

A further object, feature and advantage of the present invention is to provide a device for aid in the early detection of malignant tissue in the breasts which is portable so as to encourage its use by doctors outside their offices and by women in their own homes.

The above and other objects, features and advantages of the present invention will become more apparent from a full consideration of the following detailed description when taken in conjunction with the accompanying drawings.

DESCRIPTION OF THE PREFERRED EMBODIMENT

Figure 2:
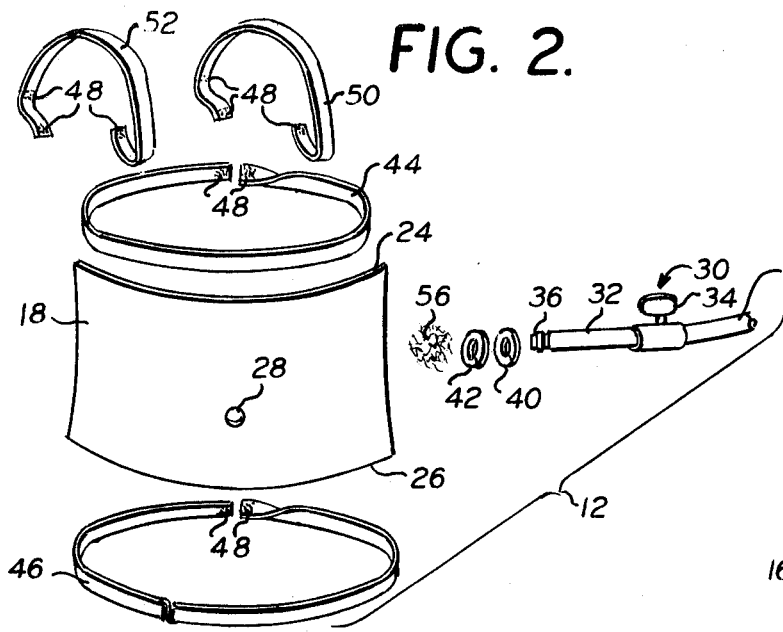
FIG. 2 is an exploded view of some of the component parts of the improved apparatus comprising the encapsulated liquid crystal film, the straps for securing the film to the woman, and the valve assembly which serves to connect the film to a vacuum source.
Figure 3:
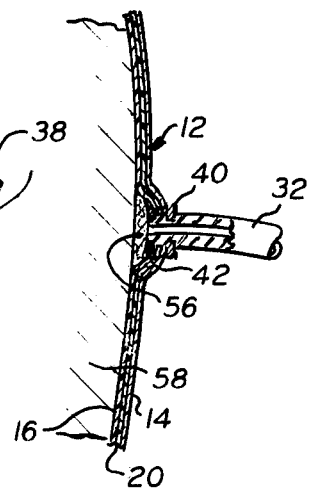
FIG. 3 is a cross-sectional view taken along line 3—3 of FIG. 1.
Figure 1:
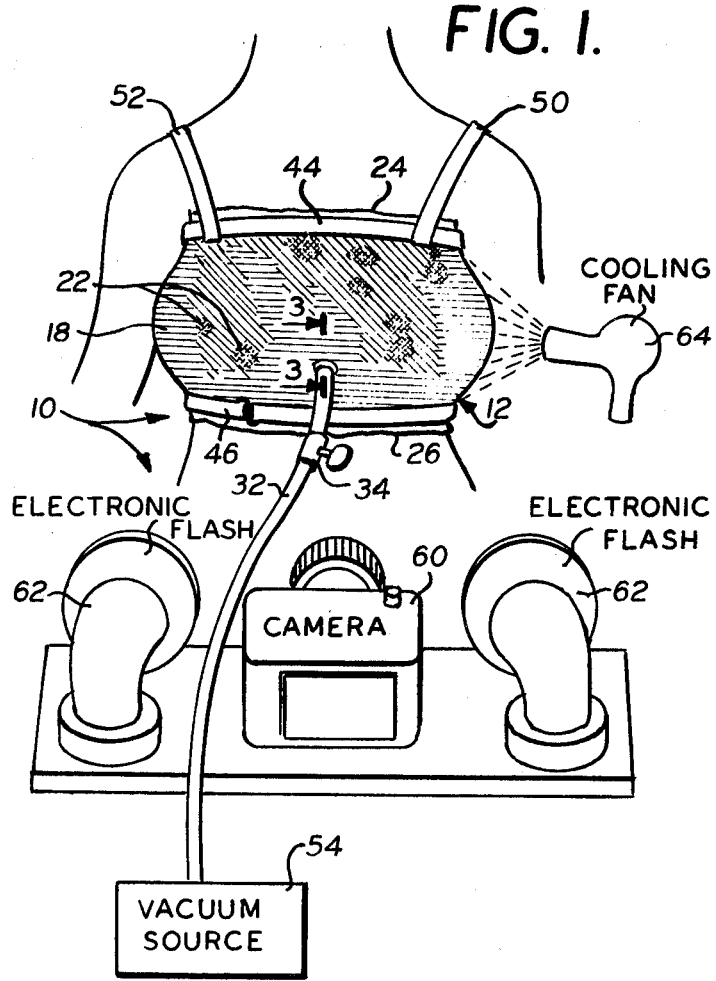
FIG. 1 is a perspective view of the improved apparatus constructed in accordance with the present invention, and illustrating the apparatus secured to the woman and in contact with the breasts to be examined.

Referring to the drawings, particularly FIGS. 1, 2 and 3, numeral 10 represents an apparatus for detecting temperature variations over selected regions of a living tissue, which apparatus is constructed in accordance with the present invention. Apparatus 10 includes a device, represented generally by numeral 12, which changes color when brought in contact with the tissue to be examined. More specifically, device 12 comprises a plurality of elastic flexible sheets 14 and 16 superimposed on each other to represent a composite film 18 having liquid crystals 20 encapsulated therebetween. The crystals 20 are responsive to changes in temperature of the tissue being examined, within a predetermined range of temperatures, to display a color pattern 22 on said film 18 representative of said temperature variations. Since the construction of the encapsulated liquid crystal film 18 (ELC) is well-known in the art, a more detailed description of the same is not deemed necessary. In this regard, attention is directed to the patents heretofore referred to in the description of the prior art for a more detailed description of the method of manufacturing such films.

Film 18 is provided with an upper edge 24 and a lower edge 26 extending longitudinally the length of the film. Film 18 is further provided with a through-opening 28 located between said upper and lower edges 24 and 26, respectively. The film is sized to wrap around the tissue being examined. For example, in the preferred use of the invention, it is intended that film 18 be wrapped around the breasts of a woman. In order to accommodate such use of the film, it is recommended that it have a dimensional figuration of 36 inches (92.3 cm) in length by 12 inches (30.7 cm) in width. It should be understood, however, that the overall dimensions of film 18 will be a function of the tissue being examined. In this regard, while the disclosed apparatus is used for detecting temperature variations over selected regions of the breasts of a woman, it will be appreciated that the apparatus may readily be used in making other clinical and physiological investigations, such as in diagnosing temperature changes in other venous and arterial blood vessels.

A valve assembly, represented generally by numeral 30, is provided having a tubular member 32 and an associated valve control 34. The valve control is located between the ends 36 and 38 of tube 32. Tube end 36 is suitably dimensioned to be received within film opening 28 to permit fluid communication between the opposite sides of film 18. In actual assembly, the tube end 36 passes through the opening 28 and projects outwardly from sheet 16 in the direction of the tissue to be examined. Tube 32 is sealingly connected to film 18 by lock nut fasteners 40 and 42, respectively engaging tube 32 from opposite sides of film 18 adjacent the tube end 36. The opposite end 38 of tube 26 is adapted to be connected to a vacuum source as hereinafter described.

FIG. 1 illustrates the film 18 secured to the patient and in contact with the breasts to be examined. The film is positioned with the longitudinally extending edges 24, 26 wrapped around the chest of the patient. It is important that the film completely encircle the tissue to be examined for reasons that will hereinafter become apparent. Film 18 is secured in place by means of a pair of elastic straps 44 and 46, respectively encircling the woman's chest. In this regard, chest strap 44 is wrapped longitudinally around film 18 adjacent its upper edge 24 and chest strap 46 is wrapped longitudinally around said film adjacent its lower edge 26. Interengaging fastening members, represented by numeral 48, are respectively affixed to the opposite ends of each of said straps 44, 46 for fastening said straps around film 18 in a stretched condition. In the preferred embodiment, the interengaging members 48 may take the form of Velcro fasteners or the like.

Film 18 may be further secured in place by means of a pair of elastic shoulder straps 50 and 52 respectively extending over a separate one of the woman's shoulders. Here again, interengaging fastening members 48 are respectively affixed to the opposite ends of each of said shoulder straps 50, 52 for fastening said shoulder straps around the chest encircling strap 44 in a stretched condition. The arrangement is such that film 18 is firmly secured to the patient with the straps 44, 46 and 50, 52 serving as a harness to engage and locate the upper and lower edges 24, 26 of film 18 firmly, yet comfortably, against the patient's skin. In other words, film 18 is secured in place with the upper and lower edges thereof in sealing contact with the regions of the chest spaced above and below the breasts to be examined. It is important that the said straps be spaced from the valve assembly 30 and from the regions of the breasts being examined to prevent deforming of said breasts during the examining procedure.

In order to insure that film 18 uniformly contacts all regions of the tissue being examined, the invention provides for evacuating air between film 18 and the breasts to cause said film to conform to the contour of the breasts without materially deforming said breasts. This is achieved by connecting the end 38 of tube 32 to a vacuum source represented by numeral 54. In order to efficiently perform the evacuating technique, a porous member 56, such as cotton or the like, is positioned between tube end 36 and the patient's skin 58, as shown in FIG. 3. The use of such porous member serves two important functions. Firstly, it prevents the skin from being sucked against tube end 36 by reason of the vacuum produced which might otherwise cause some discomfort to the patient. Secondly, it prevents the highly flexible film 18 from being collapsed against the skin in the region immediately circumscribing the opening 28. If the film were to collapse in this region, a pocket would be created which would effectively seal off the region surrounding the tube end 36 and prevent further evacuation from taking place. The cotton thus serves as a spacer or buffer to permit air to be evacuated from the space between film 18 and the patient's skin.

It has been found that the evacuation technique effectively takes place by locating tube end 36 spaced from and adjacent to the sternum of the woman's chest. The cotton member 56 is positioned in place by inserting it from the upper edge 24 of film 18 prior to the fastening of strap 44 in its stretched condition.

At such time as the air is being evacuated, it is a simple matter to prevent additional pockets from being formed between film 18 and the patient's skin by merely lifting edges 24, 26 at the location adjacent the pocket to complete the evacuating technique. This also serves to remove any wrinkles that appear on film 18 during the evacuating step. The result obtained will be to cause the ELC film to simultaneously conform to the contour of both breasts, without materially deforming said breast, and to permit a diagnostic examination of both breasts at the same time. All portions of the breasts are contacted by the film to permit a quick reliable diagnostic examination.

As previously referred to in the description of the prior art, a color pattern 22 is produced on film 18 representative of temperature variations over selected regions of the breasts. The color pattern may be observed by the doctor or by the patient standing in front of a mirror in her home. A permanent record of such color pattern may be obtained by photographically recording the pattern produced on said film to obtain a thermogram of said temperature variations. Referring to FIG. 1, the photographic record is obtained by means of camera 60 and synchronized electronic flash 62 having polarized filters.

In some applications, the initial thermographic test is followed by another test with the contoured film 18 and the breasts subjected to a cooling operation for a relatively short period of time. The cooling step is effected by a hand held cooling fan or blower as represented by number 64 in FIG. 1. The cooling-down technique may be used whenever low temperature detail is required in a specific area.

Figure 4:
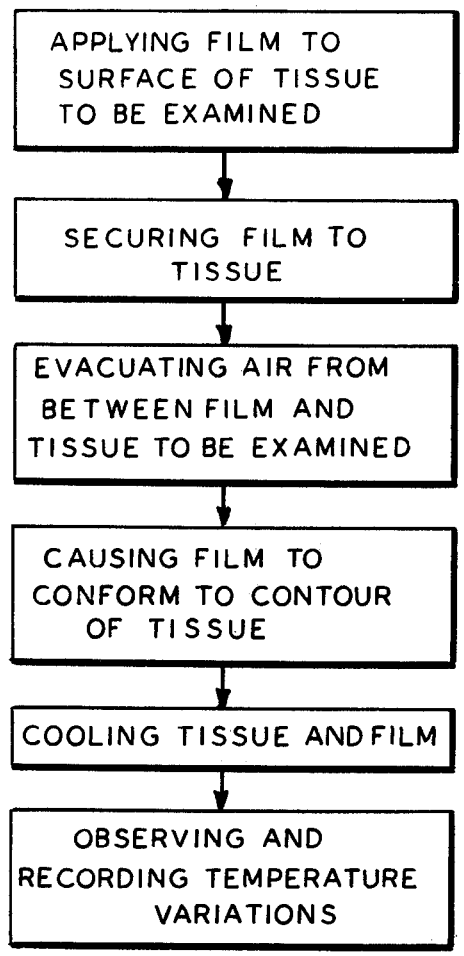
FIG. 4 is a block diagram of the steps used in practicing the invention.

FIG. 4 is a block diagram of the steps used in practicing the invention. These steps comprise the sequence of applying the film to the surface of the tissue to be examined; securing the film to the tissue; evacuating air from between the film and the tissue to be examined; causing the film to conform to the contour of the tissue; cooling the tissue and the film; and observing and recording the temperature variations.

In practicing the inventive technique, a short period of time should be permitted to lapse after the patient undresses to permit her breasts to equalize to room temperature. It is recommended that the room temperature be between 20° C. and 22° C., with all drafts being eliminated. There is no need to use air-conditioned or temperature-controlled examination rooms to practice the invention. The ELC film having the proper temperature range is then applied in contact with the breasts. The film is available in temperature ranges from 29° C. to 37° C., and film having other specific temperature ranges can be made available for higher or lower temperature applications. If the colors that appear are in the blue-green range, the temperature characteristic of the film is too low and a film having the next higher range should be selected. If the colors that appear are tan or brown, a film having the next lower range should be selected.

Once the correct film is selected, the patient places a marker on her nipples. This will enable the technician and/or the patient to know at all times where the areolar area is located. The ELC film is then wrapped around the patient and secured with the harness-like straps. The porous cotton or gauze is placed next to the sternum in the space located between the end of the tubular member and the patient's skin. The other end of the tubular member is connected to the vacuum source which is simply and conveniently a hand operated pump. The vacuum pump is then operated and if any wrinkles appear on the film during the evacuating step, the upper and lower edges of the film are lifted and re-adjusted to eliminate any pockets. At such time as the observation is completed, a photographic record may be obtained by taking one or more views of the thermo pattern produced on the film to obtain a thermograph of the temperature variations over the regions of the tissue being examined. It has been found that a highly satisfactory photographic record is obtained by the use of a flash system that is synchronized to the CU-5 Polaroid camera.

If the cooling-down step is required, the contoured film and both breasts are cooled by means of the fan or blower which is operated for approximately one minute. This serves to remove the color pattern initially produced on the film. It is recommended that a period of 30 seconds be permitted to lapse after the cooling source is removed. The doctor or patient may then re-observe the more sensitive color pattern produced on the film representative of said temperature variations.

The improved technique thus employs the use of ELC film which is readily and effectively contoured to the breasts with uniform contact by means of evacuating the air from between the film and the tissue to be examined. The technique produces a reliable full color thermo pattern of both breasts simultaneously, which pattern is recorded in full color by means of a high intensity, color balanced, polarized light system.

While a preferred embodiment of the invention has been shown and described in detail, it will be readily understood and appreciated that numerous omissions, changes and additions may be made without departing from the spirit and scope of the present invention.

We claim:

1. A method of detecting temperature variations over selected regions of the breasts of a woman within a predetermined range of temperatures, and which method utilizes liquid crystals enclosed between elastic flexible sheets which represent a composite film, and which crystals are responsive to changes in skin temperatures of said breasts to display a color pattern on said film representative of said temperature variations, said method comprising:
    (a) wrapping said film around the breasts to be examined,
    (b) securing said film in position around said breasts;
    (c) positioning a first end of a tubular member and a spacer adjacent said first end in a region spaced from the edges of said film and between said breasts, said spacer providing communication between said first end of said tubular member and the region under said film;
    (d) connecting the opposite end of said tubular member to a vacuum source;
    (e) evacuating air from between said film and said breasts;
    (f) causing said film to stretch and conform to the contour of said breasts without materially deforming said breasts; and
    (g) observing the color pattern produced on said film representative of the temperature variations over said breasts.

2. The method of claim 1 wherein said spacer is a porous material.

3. The method as recited in claim 1, further comprising the step of forming an opening in said film, said tubular member being sealingly positioned in said opening and providing fluid communication between the woman's skin and the vacuum source.

4. The method of claim 3 wherein said spacer is a porous material.

5. The method as recited in claim 1, further comprising the step of cooling said contoured film and said breasts for a relatively short period of time to remove the color pattern on said film, and then re-observing a more sensitive color pattern produced on said film representative of said temperature variations.

6. The method as recited in claim 1, further comprising the step of recording the color pattern produced on said film to obtain a thermogram of said temperature variations.

7. A method of detecting temperature variations of the breasts of a woman within a predetermined range of temperatures, and which method utilizes liquid crystals enclosed between elastic flexible sheets which represent a composite film, and which crystals are responsive to changes in skin temperatures of said breasts to display a color pattern on said film representative of said temperature variations, said method comprising:

(a) wrapping said film around the woman and in contact with the breasts to be examined;

(b) securing said film in position around said breasts;

(c) positioning one port of said tubular member in a region spaced from the edges of said film and adjacent to the sternum of the woman's chest;

(d) connecting the opposite port of said tubular member to a vacuum source;

(e) applying a porous spacer between said one port of said tubular member and the woman's skin;

(f) evacuating air from between said film and said breasts;

(g) causing said film to stretch and conform to the contour of said breasts without materially deforming said breasts;

(h) cooling said contoured film and said breasts for a relatively short period of time; and (i) observing the color pattern produced on said film representative of the temperature variations over selected regions of said breasts.

8. The method as recited in claim 7, further comprising the step of recording the color pattern produced on said film to obtain a thermogram of said temperature variations.

9. An apparatus for detecting temperature variations of the breasts of a woman within a predetermined range of temperatures, said apparatus comprising:

(a) a plurality of elastic flexible sheets superimposed on each other to represent a composite film having liquid crystals enclosed therebetween, said crystals being responsive to changes in skin temperature of said breasts to display a color pattern on said film representative of said temperature variations;

(b) securing means for securing said film in position when said film is wrapped around the breasts to be examined; and (c) a tubular member, a first end of said tubular member being located in a region spaced from the edges of said film and adapted to be positioned between said breasts, the second end of said tubular member adapted to be connected to a vacuum source for evacuating air from between said film and said breasts;

(d) said sheets having sufficient flexibility and elasticity to cause said film to stretch and conform to the contour of said breasts without materially deforming said breasts when a vacuum is drawn; and (e) a spacer located at said first end of said tubular member to prevent collapse of said flexible film around said first end of said tubular member, said spacer providing communication between said first end of said tubular member and the region under said film; whereby a color pattern is produced on said film representative of the temperature variations over regions of said breasts.

10. The apparatus of claim 9 wherein said spacer is a porous material.

11. The apparatus as recited in claim 9, wherein said film has a through-opening therein, said tubular member being sealingly positioned in said opening to provide fluid communication through said tubular member between the woman's skin and the vacuum source.

12. The apparatus of claim 11 wherein said spacer is a porous material.

13. The apparatus as recited in claim 9, wherein said film is sized to wrap around the chest of the woman, said securing means comprising first and second elastic chest encircling straps, said first strap being wrapped longitudinally along said film adjacent its upper edge and said second strap being wrapped longitudinally along said film adjacent its lower edge, and interengaging members respectively affixed to the opposite ends of each of said first and second straps for fastening said straps around the torso of the woman being examined.

14. An apparatus for detecting temperature variations of the breasts of a woman within a predetermined range of temperatures, said apparatus comprising:

(a) a plurality of elastic flexible sheets superimposed on each other to represent a composite film having liquid crystals enclosed therebetween, said crystals being responsive to changes in skin temperature of said breasts to display a color pattern on said film representative of said temperature variations;

(b) securing means for securing said film in position when said film is wrapped around the chest of the woman to be examined and in contact with the breasts to be examined, (c) said securing means comprising first and second elastic chest encircling straps, said first strap being wrapped longitudinally around said film adjacent its upper edge and said second strap being wrapped longitudinally around said film adjacent its lower edge, and interengaging members respectively affixed to the opposite ends of each of said first and second straps for fastening said straps around the torso of the woman being examined;

(d) vacuum means for evacuating air between said film and said breasts; said vacuum means comprising a vacuum source, a valve assembly having a tubular member connected to said film and a vacuum source, one end of said tubular member being located in a region spaced from the edges of said film and adapted to be positioned adjacent to the sternum of the woman's chest, the opposite end of said tubular member being connected to said vacuum source;

(e) said sheets having sufficient flexibility and elasticity to cause said film to stretch and conform to the contour of said breasts without materially deforming said breasts when a vacuum is drawn; and (f) a porous spacer positioned adjacent said one end of said tubular member to prevent collapse of said flexible film around said one end of said tubular member;

whereby a color pattern is produced on said film representative of the temperature variations over selected regions of said breasts.

15. The apparatus as recited in claim 14, wherein said film has a through-opening therein, said tubular member being sealingly positioned in said opening and providing fluid communication between the woman's skin and the vacuum source.

16. The apparatus as recited in claim 14, wherein said film securing means further comprises first and second elastic shoulder straps each extending over a separate one of the shoulders of the woman, and interengaging members respectively affixed to the opposite ends of each of said first and second shoulder straps for fastening said shoulder straps around said first chest encircling strap.

* * * * *